United States Patent
DeBusk et al.

(10) Patent No.: US 9,990,466 B2
(45) Date of Patent: Jun. 5, 2018

(54) AUTOMATED SYSTEM FOR MEDICAL ITEM DISPENSING, BILLING, AND INVENTORY MANAGEMENT

(75) Inventors: Brian C. DeBusk, Knoxville, TN (US); Angela M. Sewell, Knoxville, TN (US); Gregory S. Hodge, Knoxville, TN (US); Samuel J.E. Fox, Oliver Springs, TN (US)

(73) Assignee: DeRoyal Industries, Inc., Powell, TN (US)

( * ) Notice: Subject to any disclaimer, the term of this patent is extended or adjusted under 35 U.S.C. 154(b) by 454 days.

(21) Appl. No.: 13/546,324

(22) Filed: Jul. 11, 2012

(65) Prior Publication Data

US 2014/0337049 A1    Nov. 13, 2014

Related U.S. Application Data

(63) Continuation-in-part of application No. 13/223,641, filed on Sep. 1, 2011, now Pat. No. 8,818,824, which
(Continued)

(51) Int. Cl.
*G06Q 50/10* (2012.01)
*G06F 19/00* (2018.01)
(Continued)

(52) U.S. Cl.
CPC .......... *G06F 19/327* (2013.01); *G06F 19/328* (2013.01); *G06F 19/3462* (2013.01); *G06Q 10/087* (2013.01); *G07F 17/0092* (2013.01)

(58) Field of Classification Search
CPC ...... G06Q 50/22; G06Q 50/24; G06Q 10/087; G06Q 10/08; G06F 19/3456; G06F 19/322; G06F 19/3462
See application file for complete search history.

(56) References Cited

U.S. PATENT DOCUMENTS

| | | | | |
|---|---|---|---|---|
| 5,671,362 A | * | 9/1997 | Cowe | G06Q 10/087 340/5.92 |
| 6,604,019 B2 | * | 8/2003 | Ahlin et al. | 700/231 |

(Continued)

OTHER PUBLICATIONS

Wavemark, Inc., Intelligent Storage Units & Usage Tracking, Brochure, pp. 1-2, USA, www.wavemark.net/website/documents/cabinetspecs.pdf.
(Continued)

*Primary Examiner* — Lena Najarian
(74) *Attorney, Agent, or Firm* — Luedeka Neely Group, P.C.

(57) ABSTRACT

An inventory management system provided by an inventory management service provider senses removal of medical items from inventory to be dispensed to a patient. The system processes billing information to identify the patient's medical insurance provider, to identify a medical item supplier that is the preferred biller for the patient's medical insurance provider, and to determine whether the inventory management service provider is the identified preferred biller. If the inventory management service provider is the preferred biller, the system generates an invoice from the inventory management service provider to bill the patient's medical insurance provider. If the inventory management service provider is not the preferred biller, the system sends the billing information to the medical item supplier identified as the preferred biller, and generates a billing-only invoice directed to the medical item supplier identified as the preferred biller, which invoice is remit to the inventory management service provider.

3 Claims, 6 Drawing Sheets

Related U.S. Application Data is a continuation-in-part of application No. 13/448,732, filed on Apr. 17, 2012, now abandoned.

(51) Int. Cl.
*G06Q 10/08* (2012.01)
*G07F 17/00* (2006.01)

(56) References Cited

U.S. PATENT DOCUMENTS

| | | | |
|---|---|---|---|
| 2002/0032582 A1 | 3/2002 | Feeney, Jr. et al. | |
| 2004/0084526 A1* | 5/2004 | Knowles | G06Q 10/087 235/385 |
| 2006/0259377 A1* | 11/2006 | Fedor et al. | 705/28 |
| 2009/0027164 A1* | 1/2009 | Hara | 340/10.1 |
| 2010/0094649 A1* | 4/2010 | White | 705/2 |
| 2010/0106515 A1* | 4/2010 | McCoy | 705/2 |
| 2010/0138238 A1* | 6/2010 | Sobie | 705/3 |
| 2010/0141457 A1* | 6/2010 | Wass | G06Q 10/08 340/572.8 |
| 2010/0198611 A1* | 8/2010 | Ruoff et al. | 705/2 |
| 2010/0262432 A1* | 10/2010 | Benja-Athon | 705/2 |
| 2011/0010275 A1* | 1/2011 | Hull | 705/28 |
| 2011/0077969 A1* | 3/2011 | Zhu et al. | 705/3 |
| 2011/0173028 A1* | 7/2011 | Bond | G06Q 10/08 705/3 |
| 2011/0202170 A1 | 8/2011 | Dawes et al. | |
| 2012/0203566 A1* | 8/2012 | Kidd | G06Q 50/22 705/2 |

OTHER PUBLICATIONS

Wavemark, Inc., Clinical Inventory Management Solution, Brochure, pp. 1-4, USA, www.wavemark.net/website/documents/wavemarkbrochure.pdf.

European Search Report, European Patent Application No. 12828774, dated Mar. 3, 2015, 10 pages.

* cited by examiner

AUTOMATED SYSTEM FOR MEDICAL ITEM DISPENSING, BILLING, AND INVENTORY MANAGEMENT

This application is a continuation-in-part of and claims priority to co-pending U.S. patent application Ser. No. 13/223,641 filed Sep. 1, 2011, and Ser. No. 13/448,732 filed Apr. 17, 2012, both titled AUTOMATED SYSTEM FOR MEDICAL ITEM DISPENSING, BILLING, AND INVENTORY MANAGEMENT.

FIELD

This invention relates to an inventory management system. More particularly, this invention relates to a system for managing inventories of medical supply items.

BACKGROUND OF THE INVENTION

Durable Medical Equipment (DME), Prosthetics, Orthotics and Supplies (DMEPOS) as defined by the Department of Health and Human Services and its Center for Medicare Services (CMS) is a class of medical devices, products and supplies that are typically reimbursable under Part B of the U.S. Medicare health care program. In general, this category of products includes items provided to patients who receive outpatient treatment for certain health problems that do not require inpatient admission to a hospital or other healthcare institution. DMEPOS items are typically provided or prescribed to help alleviate, treat or assist in recovery from the condition that prompted the outpatient treatment of the patient. Such outpatient treatment can occur in any number of settings, such as a hospital emergency department, a clinic, or a physician's or therapist's office.

In general, the costs of DMEPOS items are reimbursable or payable separately from the healthcare professional's fee for treatment of the patient. DMEPOS items are typically reimbursable or payable in both Medicare and Medicaid programs and through private health insurers. Traditionally, most DMEPOS items were prescribed by the treating professional and those prescriptions could be filled by DME shops, Orthotics/Prosthetics shops, pharmacies with DME services, etc. However, as a convenience to patients many healthcare providers would like to dispense DMEPOS items at the time of treatment of the patient in order to facilitate patient convenience and continuity of care.

Since DMEPOS items are typically reimbursable or payable under a different billing and reimbursement system than professional healthcare services, it has been difficult for healthcare professionals to provide the dispensing of these items as an adjunct service to their patients. The specialty shops that have traditionally dispensed these items have developed the business processes necessary to properly stock the products, manage the inventory, properly associate prescriptions for DMEPOS items with appropriate coding under the CMS coding system, generate the regulatory paperwork for delivery of the item to the patient and generate the necessary forms for submission to the reimbursement agency such as Medicare, Medicaid, or private insurance.

Healthcare providers have a need to dispense DMEPOS items as an adjunct service to their medical practice, without having to individually develop all of the business processes which suppliers have developed previously and without the labor and overhead costs associated with those types of suppliers. Healthcare providers need to be able supply the patient with DMEPOS products that the healthcare provider has evaluated and knows to be appropriate for the patient's particular diagnosis and indications. It would be a significant advantage for the patient if the healthcare provider could provide the DMEPOS item at the time of initial diagnosis and treatment of the patient. This would allow the healthcare provider to properly fit the item to the patient and instruct the patient on the proper use of the item. For the patient, this would minimize the hassle of having to go to other locations to complete the diagnosis and treatment, and would generally result in better continuity of care.

SUMMARY OF THE INVENTION

The above and other needs are met by an integrated and automated medical product/supply dispensing, billing and inventory management system for use in the health care environment. The system includes several core functional software applications that communicate either through a networked information system architecture, or which reside on a single, general purpose computer workstation. In addition to the information system applications, the system includes a product/supply inventory management system which in general provides limited access to certain medical products or supplies and captures key information in the course of dispensing those products or supplies that subsequently enables the inventory management and billing functions of the system to operate.

Some preferred embodiments provide an inventory management system for managing information regarding medical items dispensed in conjunction with medical treatment of patients of a medical facility. The inventory management system is provided by an inventory management service provider that is also a supplier of medical items that are dispensed. The inventory management system includes inventory sensors that sense removal of medical items from an inventory space of the medical facility to be dispensed to a patient. One or more computers that are in communication with the inventory sensors are configured to store and manage item usage information and billing information for medical items dispensed to patients. The billing information includes information regarding the patients, medical insurance providers and medical item suppliers. The billing information also includes information that associates each of the patients with a medical insurance provider to which medical expenses incurred by the patent are to be billed. The billing information further includes information that associates each medical insurance provider with a medical item supplier that is a preferred biller for the medical insurance provider.

The inventory management system includes software applications comprising sets of computer-executable instructions which, when executed:
associate the item usage information with patient information that identifies the patient to which the one or more medical items are dispensed;
process the billing information to identify the patient's medical insurance provider;
process the billing information to identify the medical item supplier that is the preferred biller for the patient's medical insurance provider;
determine whether the inventory management service provider is the medical item supplier identified as the preferred biller for the patient's medical insurance provider;
generate an invoice from the inventory management service provider to bill the patient's medical insurance provider when it is determined that the inventory management service provider is the preferred biller for the patient's medical insurance provider; and send the billing information to the medical item supplier identified as the preferred biller for the patient's medical insurance provider when it is determined that the inventory management service provider is not the preferred biller for the patient's medical insurance provider.

In some embodiments of the inventory management system, when it is determined that the inventory management service provider is not the preferred biller for the patient's medical insurance provider, the computer-executable instructions also generate a billing-only invoice directed to the medical item supplier identified as the preferred biller for the patient's medical insurance provider. The billing-only invoice is remit to the inventory management service provider.

In another aspect, the invention provides a computer-implemented method for managing information regarding medical items dispensed in conjunction with medical treatment of patients at a medical facility. In preferred embodiments, one or more steps of the method are performed on a computer system of an inventory management service provider that is also a medical item supplier. The method includes the following steps:

(a) storing in a computer storage device billing information regarding medical items dispensed to patients of the medical facility, where the billing information indicates an association between each patient and a medical insurance provider to which the patient's medical expenses are to be billed, and the billing information further indicates an association between each medical insurance provider and a medical item supplier that is a preferred biller for the medical insurance provider;

(b) sensing removal of medical items from an inventory space of the medical facility to be dispensed to a patient, where the sensing is performed using inventory sensors disposed in the inventory space of the medical facility;

(c) generating item usage information indicative of an identity and quantity of the medical items removed;

(d) associating the item usage information with patient information that identifies the patient to which the medical items are dispensed;

(e) processing the billing information to identify the medical insurance provider of the patient to which the medical items are dispensed;

(f) processing the billing information to identify the medical item supplier that is the preferred biller for the medical insurance provider identified in step (e);

(g) determining whether the inventory management service provider is the medical item supplier identified in step (f);

(h) when it is determined that the inventory management service provider is the medical item supplier identified in step (f), generating an invoice from the inventory management service provider to bill the medical insurance provider identified in step (e); and (i) when it is determined that the inventory management service provider is not the medical item supplier identified in step (f), sending the billing information to the medical item supplier identified in step (f).

In some embodiments, when it is determined that the inventory management service provider is not the medical item supplier identified in step (f), a billing-only invoice is generated for the medical item supplier identified in step (f), where the billing-only invoice is remit to the inventory management service provider.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION OF EMBODIMENTS OF THE INVENTION

Figure 4:
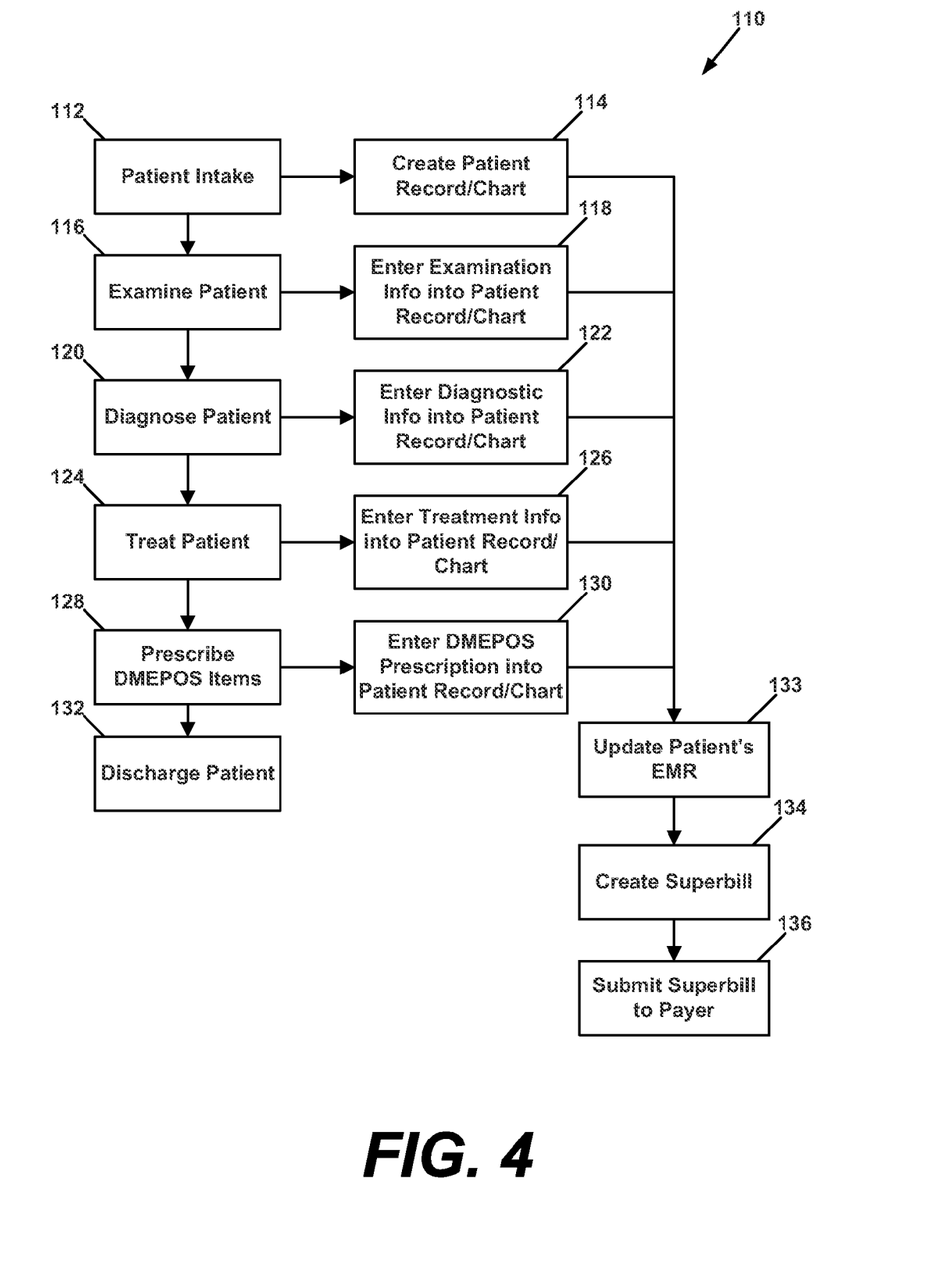
FIG. 4 depicts a typical workflow for the provision of DMEPOS items based on traditional practices.

A typical workflow for the provision of DMEPOS items under traditional practices is depicted in FIG. 4. Generally, a patient follows a treatment path 110 which typically begins with the patient arriving at a treatment facility with a medical condition and ends with the patient being discharged or leaving the treatment facility. Examples of treatment facilities include a hospital emergency department, a physician's office, a clinic, and a therapy office. The first step in the treatment path 110 is typically patient intake (step 112) in which information concerning the patient is recorded and a patient record/chart (or face sheet) is created as an output (step 114). Typically, patient intake (step 112) includes collecting of basic demographic and medical information about the patient, as well as payment responsibility information, such as insurance information (either private insurance or information regarding participation in a government program such as Medicare/Medicaid). This information is recorded in the patient record/chart, which is typically created in electronic form in a pre-existing information system resident in the treatment facility.

Following patient intake (step 112) is the examination of the patient (step 116). In this step, the appropriate healthcare provider examines the patient, takes a patient history, and reviews the symptoms. The examination (step 116) may also include other diagnostic activities such as lab work and imaging that assist the provider in making an accurate diagnosis. Examination information is typically recorded into the patient record/chart (step 118). The healthcare provider then makes a diagnosis of the patient (step 120), and the diagnostic information is also entered into the patient record/chart (step 122).

After diagnosis (step 120) and entering the diagnostic information in the patient record/chart (step 122), the next step is typically treatment of the patient (step 124). In the context of this invention, treatment of the patient typically includes the healthcare provider prescribing or providing a DMEPOS item, such as an orthotic, to facilitate treatment of the diagnosed condition (step 128). Information regarding the treatment, including DMEPOS prescription information, is entered into the patient record/chart (steps 126 and 130), and this information is entered in the patient's Electronic Medical Records (step 133).

The final step in the treatment Path 110, is for the patient to be discharged or released (step 132). The information entered into the patient record/chart at each step in the treatment path 110 is used to supply information to create a medical complaint bill reflecting all of the billable services provided in the process (step 134). This information is then uploaded to the appropriate billing software for submittal to payer (step 136).

Figure 1:
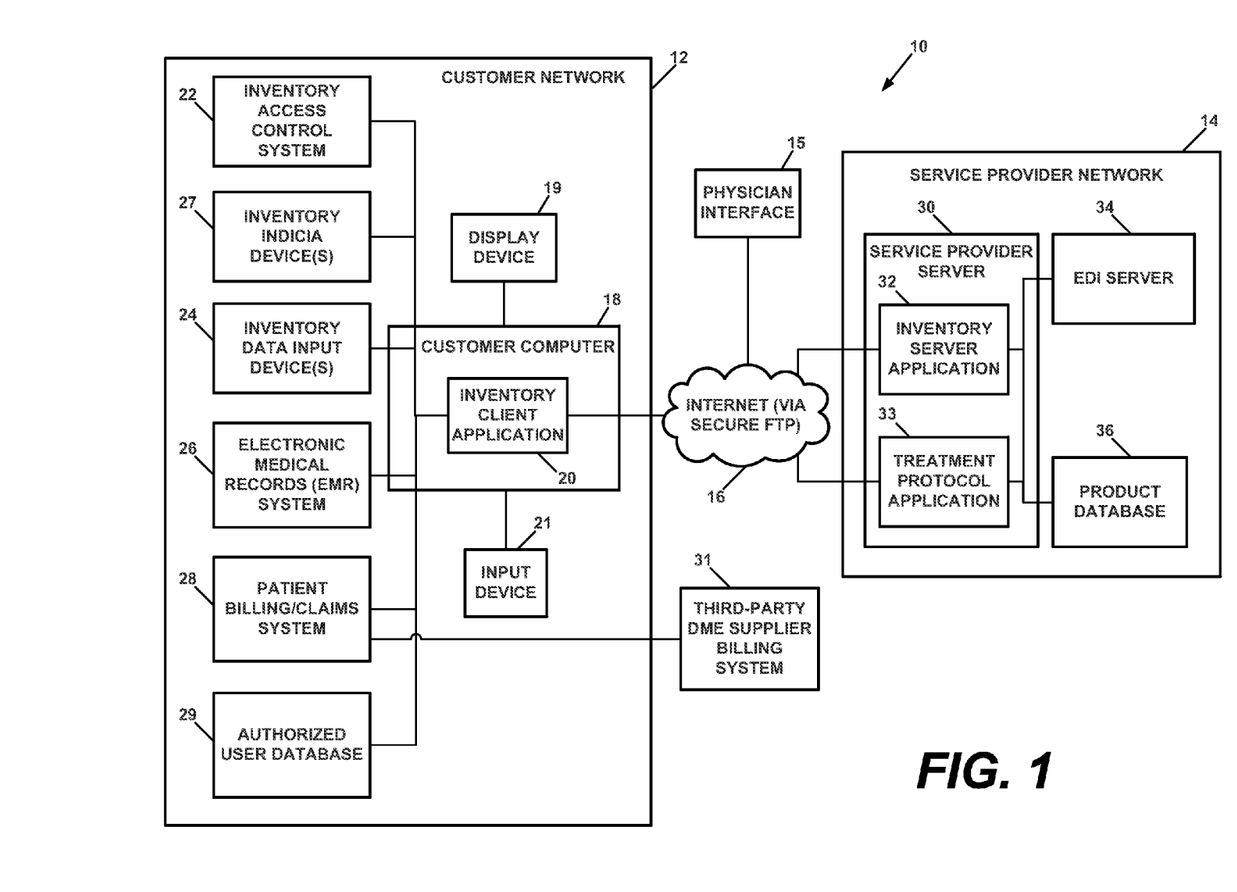
FIG. 1 is a functional block diagram of an embodiment of a medical product/supply dispensing, billing and inventory management system.

FIG. 1 depicts an embodiment of a medical product/supply dispensing, billing and inventory management system 10. As described in more detail hereinafter, the system 10 provides computer-implemented tools and processes for managing an inventory of medical products/supplies, for dispensing such products/supplies to patients, and for billing a payer for the dispensed products/supplies. However, one skilled in the art will recognize that the system 10 may be used to manage inventories of other components and materials in medical and nonmedical applications. Thus, the embodiments described herein are not limited only to medical product/supply inventory, dispensing, and billing applications.

As shown in FIG. 1, the system 10 includes a customer computer network 12 and a service provider computer network 14 which communicate with each other via a communication network 16 such as the Internet. As the term is used herein, "customer" generally refers to a medical facility where medical diagnostic and treatment procedures are performed, such as a hospital, outpatient surgical center, physician's office, clinic, or therapy office. The term "customer" may also refer to any consumer of products/supplies that are inventoried and managed using the system described herein. Accordingly, one or more of the components of the customer computer network 12 may be located within a hospital, clinic, doctor's office, or other medical facility.

The customer computer network 12 includes a customer computer 18 that is operable to communicate through the Internet 16 with the service provider computer network 14. The customer computer 18 may be, for example, a desktop computer, laptop computer, tablet computer, or smart phone. An inventory client application 20 is loaded on the customer computer 18 to provide some or all of the inventory management, dispensing, and billing functions described herein. The customer computer 18 and the client application 20 are in communication with an inventory access control system 22, one or more inventory sensors 24, an Electronic Medical Records (EMR) computer system 26, and a patient billing/claims computer system 28. A user input device 21, such as a keyboard or mouse or touchpad, is preferably provided as a component of the customer computer 18. In a preferred embodiment, the customer computer 18 also includes a display device 19 within the inventory space on which the inventory client application 20 displays information regarding inventory transactions. In some embodiments, the display device 19 and user input device 21 are combined as a touch screen device.

Figure 6:
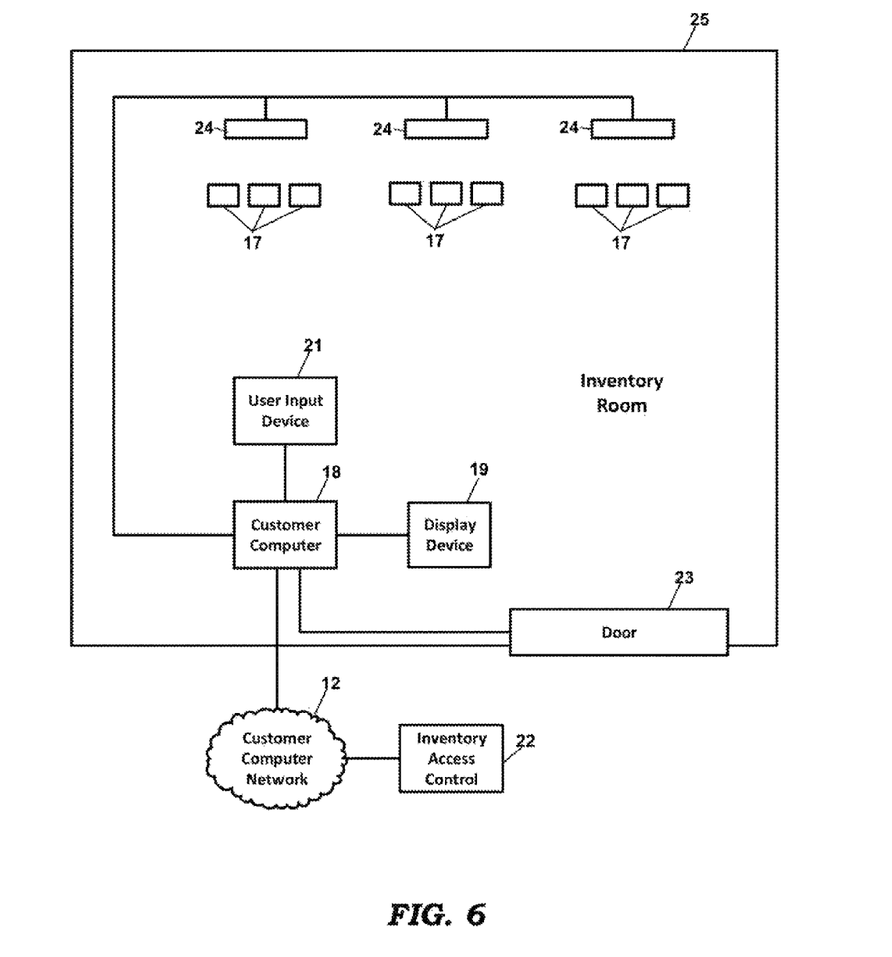
FIG. 6 depicts a functional block diagram of an inventory space having a door, and components of a medical product/supply dispensing, billing and inventory management system.

As depicted in FIG. 6, the inventory access control system 22 comprises a keypad, magnetic stripe reader (card swipe), proximity reader, RFID tag reader, biometric sensor device, a digital camera and facial recognition software, or other entry-access device that authorized customer personnel use to gain access to a medical product/supply inventory space 25. The inventory space 25 may be a secured, limited-access location in the customer facility in which DMEPOS items 17 are stored. In preferred embodiments, the inventory access control system 22 communicates with the customer computer 18 via a wired or wireless network connection.

As the term is used herein, an "inventory space" 25 may be a secured, limited access inventory room or supply room as shown in FIG. 6. Alternatively, an inventory space 25 may be a storage structure, such as cabinet, box, cage or other enclosure. In some embodiments, multiple inventory spaces may be provided in a single room. For example, there may be one secured cabinet containing DMEPOS items and another secured cabinet in the same supply room containing surgical implant items. In some embodiments, the inventory space may be an unsecured space into which anyone may enter or gain access.

As the term is used herein, a "storage container" may be a bin, drawer, shelf or other receptacle in which medical items are stored. Typically, there are multiple storage containers in an inventory space.

The inventory sensors 24 are devices which sense the removal or addition of DMEPOS items from or to the inventory space. In one embodiment, the inventory sensors 24 are weight sensors attached to storage bins within the inventory space. In this embodiment, the inventory sensors 24 sense that one or more items have been added to a bin based on an increase in weight of the bin, and that one or more items have been removed from the bin based on a decrease in weight of the bin. With this system, particular bins are designated to hold particular items, so that a change in weight of the bin can be associated with a change in inventory of the corresponding item.

In another embodiment as depicted in FIG. 6, the inventory sensors 24 are RFID sensors which sense the presence of RFID tags attached to DMEPOS items 17 within the inventory space 25. When an RFID tag on an item 17 is within range of the RFID sensors 24, the tagged item is designated as being in inventory. Conversely, when the RFID tag on an item 17 is outside the range of the RFID sensors, the tagged item is designated as being removed from inventory. In this embodiment, since the RFID tags identify the items 17 to which they are attached, there is no need to designate particular bins or locations for each item 17 within the inventory space 25.

In another embodiment, the inventory sensors 24 are RFID sensors which sense the presence of RFID tags attached to DMEPOS items when in range of the sensors. When an RFID tag on an item is within range of the RFID sensors, the tagged item is designated as being removed from inventory. Conversely, when the RFID tag on an item is outside the range of the RFID sensors, the tagged item is designated as being in inventory. In this embodiment, since the RFID tags identify the items to which they are attached, there is no need to designate particular bins or locations for each item within the inventory space.

In yet another embodiment, the inventory sensors 24 comprise one or more digital imaging devices, such as still cameras or video cameras, that capture images of items as the items are removed from or placed into the inventory space. In this embodiment, each item is marked with a distinctive identifier, such as a bar code, QR code, or other symbol, that uniquely identifies the item. The imaging devices are positioned such that their field of view will encompass an area through which items must pass as the items are removed from or added to the inventory space. Movement within the field of view triggers the imaging devices to capture multiple images of the items, such that at least one of the captured images may show the distinctive identifier on each item. Software executed on the customer computer 18, either as a module of the inventory client application 20 or a separate application, processes the image of the distinctive identifier (such as by "reading" the bar code or QR code) and provides identification information indicating which item is captured in the image.

In the embodiments discussed above, the inventory sensors 24 are substantially automatic. That is, they detect the addition and removal of items to and from inventory without human interaction. In a third embodiment, human interaction is required. In this embodiment, the inventory sensors 24 are barcode readers, and when a DMEPOS item is added to or removed from inventory, this is logged by scanning a barcode attached to the item.

The EMR computer system 26 comprises one or more computers that store and manage records regarding the status of patients receiving treatment in a medical facility. Generally, a patient's status is either admitted to the facility, discharged from the facility, or transferred to another department, location or facility.

In preferred embodiments, an inventory indicia device 27 is provided for each bin, shelf or drawer in the inventory space. These devices 27 preferably comprise an LED or LCD or other lighted display device disposed adjacent each bin, shelf and drawer. Depending on the current mode of operation, these devices 27 may provide a display of the number of items currently in each associated bin, shelf or drawer, or they may display a number of items that are to be added to the associated bin, shelf or drawer during a replenishment process as describe in more detail hereinafter. These indicia devices 27 are preferably controlled by the customer computer 18 based on the executed instructions of the inventory application 20.

The billing/claims computer system 28 comprises one or more computers that store and manage records regarding the billing for services rendered and DMEPOS items dispensed in examining, diagnosing, and treating patients. In preferred embodiments, this system 28 generates bills (in paper or electronic form) which are sent to patients, and generates claims which are sent to private insurers and Medicare/Medicaid. In some embodiments, the billing/claims computer system 28 is operable to communicate with a billing computer system 31 of a third-party DME supplier, such as through a secure Internet connection. As the term is used herein, a "third-party DME supplier" is any DME supplier other than the "Service Provider" which is the supplier entity that maintains the service provider computer network 14.

With continued reference to FIG. 1, the service provider computer network 14 comprises one or more computers which store information and execute software for medical product/supply dispensing, billing and inventory management. As the term is used herein, a "Service Provider" may be a company that maintains inventories of DMEPOS items that are supplied to the customer to be dispensed to patients. An example of one such Service Provider is DeRoyal Industries, Inc. of Powell, Tenn. Alternatively, the Service Provider may not maintain the inventory, but may provide inventory management services for another company that does maintain the inventory.

In the embodiment of FIG. 1, the service provider computer network 14 includes an inventory management server computer 30 running an inventory server application 32, an electronic data interchange (EDI) server 34, and a product inventory database 36. The EDI server 34, which may be a J.D. Edwards/Oracle server, executes programs for implementing electronic commerce transactions between the service provider network 14 and the customer network 12. The product inventory database 36 stores records indicating quantities, coding, use and application of each DMEPOS item in the Service Provider's inventory.

Figure 2:
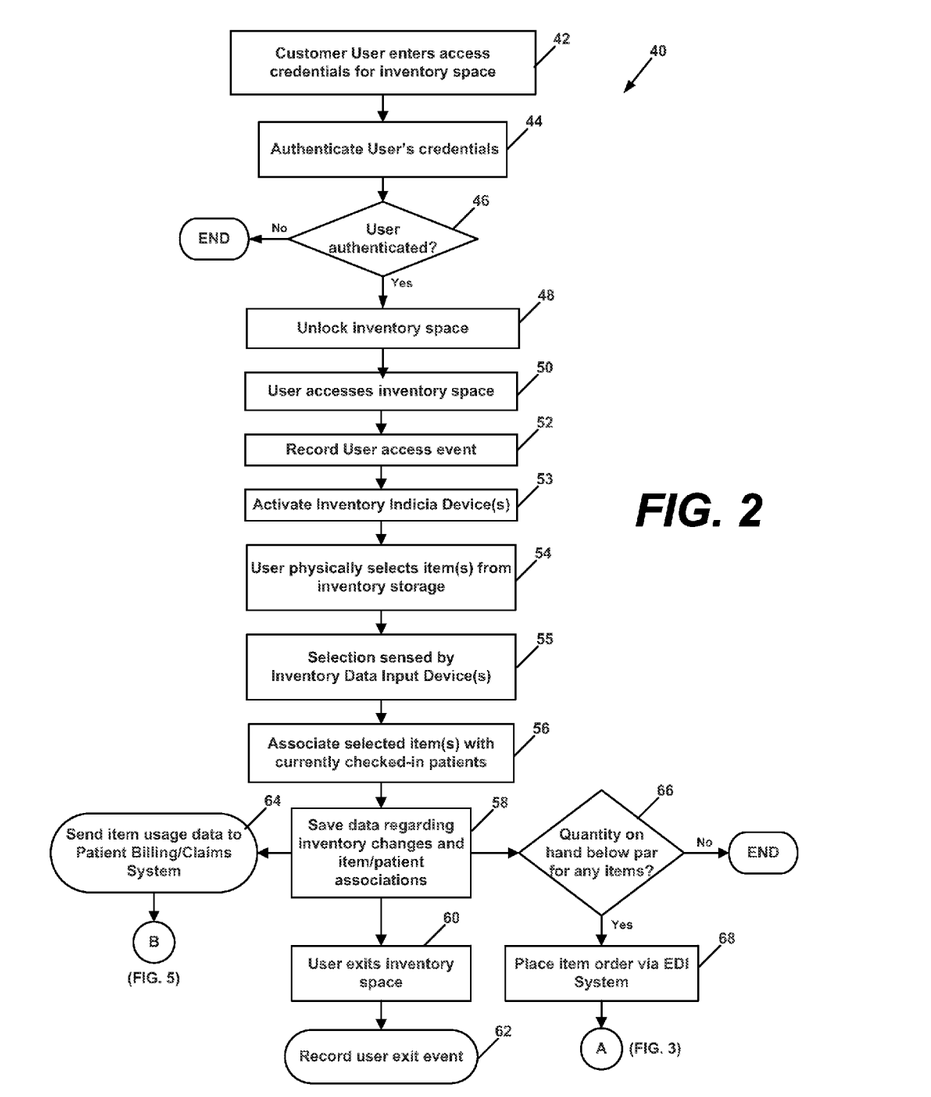
FIGS. 2 and 3 are flowcharts describing the operation of an embodiment of a medical product/supply dispensing, billing and inventory management system.

FIG. 2 and FIG. 6 depict a process 40 for providing access to DMEPOS items 17 in the inventory space 25 of the customer facility, for logging removal of inventory items 17, and for billing the patient accordingly. Generally, the process 40 begins when a customer user enters credentials for gaining access to the inventory space 25 (step 42). In one embodiment, this is accomplished by swiping a magnetic stripe on an ID card through a card reader of the inventory space access control system 22 (FIG. 1 and FIG. 6). In another embodiment, this is accomplished by swiping a proximity card near a proximity reader. In another embodiment, this involves passing an RFID tag near an RFID reader. In another embodiment, this involves entering a code on a keypad. In yet another embodiment, this involves a retina scan or a thumbprint scan using a biometric scanning device. In still another embodiment, this involves capturing an image of the user's face with a digital camera and processing the image using facial recognition software.

After entry of the customer user's credentials, the inventory client application 20 running on the customer computer 18 authenticates the credentials (step 44), such as by comparing the credentials to records saved in an authorized user database 29. The authorized user database 29 may be maintained on the customer network 12 or on the service provider network 14.

If the user's credentials are not authenticated (step 46), the door 23 of the inventory space 25 remains locked and no further action is taken, other than to log a failed entry attempt. If the user's credentials are authenticated, the inventory client application 20 executes a command to unlock the door 23 or other access port to the inventory space 25 (step 48) and the user may access the space 25 (step 50). The inventory client application 20 then updates a user entry log to record this user access event, with the date and time of access and the name/ID number of the user (step 52). Additionally, the user is logged into the application 20.

In some embodiments, the inventory indicia devices 27 are activated to display to the user the quantity of each item that is to be removed from each bin, shelf or drawer in the inventory space, and the number is automatically decremented as the items are removed (step 53).

When the user selects one or more items from the shelves, bins, or drawers of the inventory space (step 54), the selection is sensed by one or more of the inventory sensors 24 and corresponding selection data is provided to the inventory client application 20 (step 55). In a preferred embodiment, a list of the selected items is then displayed on the display screen 19 for viewing by the user. In situations wherein a bill of material (BOM) has been generated for refilling a procedural tray or other kit of items and the BOM has been accessed by the inventory client application 20, the sensors 24 sense whether the correct number of items have been removed from the shelves, bins or drawers as indicated by the BOM.

Using the input device 21, the user inputs information that the inventory client application 20 uses to associate each selected item with a currently admitted or checked-in patient in the facility (step 56). To input this information, the user may select the patient's name from a list displayed on the display device 19, which list is generated from data accessed from the EMR computer system 26. Alternatively, the user may scan a barcode assigned to the patient which is attached to the patient's paperwork. In other embodiments, the patient is associated with the selected DMEPOS item by patient information included in RFID tag on the patient's chart.

The inventory client application 20 saves data regarding the removal of items from inventory (also referred to as item usage data) and data indicating the item/patient association (step 58). The item usage data and item/patient association data are sent to the patient billing/claims computer system 28 for further processing (step 64). For example, the patient billing/claims computer system 28 may use this data to submit claims for payment to appropriate insurance providers.

Figure 5:
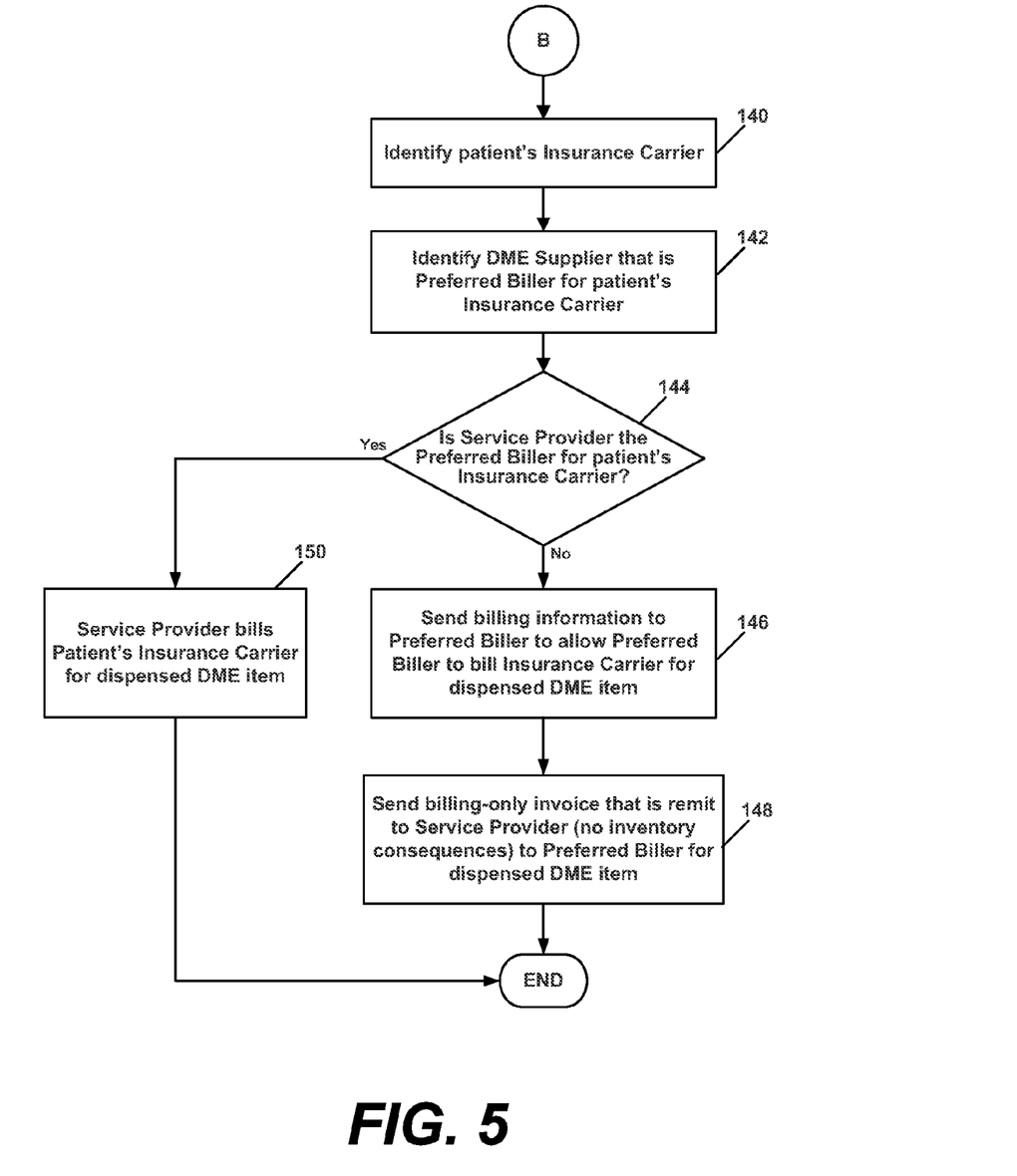
FIG. 5 depicts a flowchart describing the processing of billing information related to a dispensed DME item.

In one preferred embodiment, the patient billing/claims computer system 28 executes a billing process as depicted in FIG. 5. First, the patient's insurance carrier is identified (step 140). This determination may be made based on patient records stored in the EMR computer system 26 (FIG. 1). The system then identifies the DME supplier that is the preferred biller for the patient's insurance carrier (step 142). Table I provides an example listing of insurance carriers in association with their preferred biller DME suppliers. For example, DeRoyal Continuum is the DME supplier that is the preferred biller for Blue Cross Blue Shield. Information associating insurance carriers and preferred billers may be stored in a database connected to the customer network 12 or the service provider network 14 or both.

TABLE I

| Insurance Carrier | DME Supplier |
| --- | --- |
| Blue Cross Blue Shield | DeRoyal Continuum |
| Humana | Bob Jones Medical Supply |
| Medicare | Lambert's Health Care |
| Other insurance carrier | Other DME supplier |

As shown in FIG. 5, if the Service Provider is the DME supplier that is the preferred biller for the patient's insurance carrier (step 144), the Service Provider bills the insurance carrier for the dispensed DME item (step 150). If the Service Provider is not the preferred biller for the patient's insurance carrier (step 144), billing information for the dispensed item is sent to the preferred biller so the preferred biller can bill the patient's insurance carrier (step 146). The billing information may be on a one-page document that provides the patient demographics, insurance carrier information and dispensed DME. A billing-only invoice that is remit to the Service Provider (no inventory consequences) is also sent to the preferred biller for the dispensed DME item (step 148).

Consider the following example. DeRoyal Continuum is the Service Provider for Tennova Healthcare. A low-profile walker is dispensed to John Smith, a patient of Tennova. Blue Cross Blue Shield is John Smith's insurance carrier. Since DeRoyal Continuum is the preferred biller for Blue Cross Blue Shield, DeRoyal Continuum submits a bill to Blue Cross Blue Shield for the low-profile walker.

Now consider an example in which a knee brace is dispensed to Susan White, also a patient of Tennova. Susan's insurance carrier is Humana, and Bob Jones Medical Supply is the preferred biller for Humana. In this situation, since DeRoyal Continuum is the Service Provider, but not the preferred biller, all billing information is sent to Bob Jones Medical Supply so that Bob Jones can bill Humana for the knee brace. A billing-only invoice is also sent to Bob Jones and is remitted to DeRoyal Continuum for the knee brace.

With reference again to FIG. 2, based on the item usage data, the inventory client application 20 determines whether the remaining quantity of inventory items is below a predetermined minimum threshold (step 66). If so, the inventory client application 20 places an order for some quantity of the items via the Internet connection to the Service Provider's EDI server 34 (step 68). Alternatively, the inventory client application 20 sends an email or other electronic message to the person responsible for maintaining the inventory to remind the person to place an order.

After the user has associated the items taken from inventory with one or more patients (step 56), the user may exit the inventory space (step 60) and the inventory client application 20 logs a user exit event (step 62). In some embodiments wherein the inventory space is a room or cage, the inventory room door may not be opened to allow the user to exit until the user has done whatever is needed to complete item/patient association (step 56). In other embodiments, the door may be opened, but if the item/patient association has not been completed beforehand, an alarm sounds to remind the user to complete that task before leaving. In some embodiments, if the user leaves the inventory space without completing the item/patient association, the user will receive an email or text message reminding the user to complete the task.

By logging user access and exit events, the system 10 keeps track of all users that access the inventory space, and it associates the items removed from or added to inventory with the dates/times that each user accessed the inventory space. This provides for user accountability in the inventory process.

Figure 3:
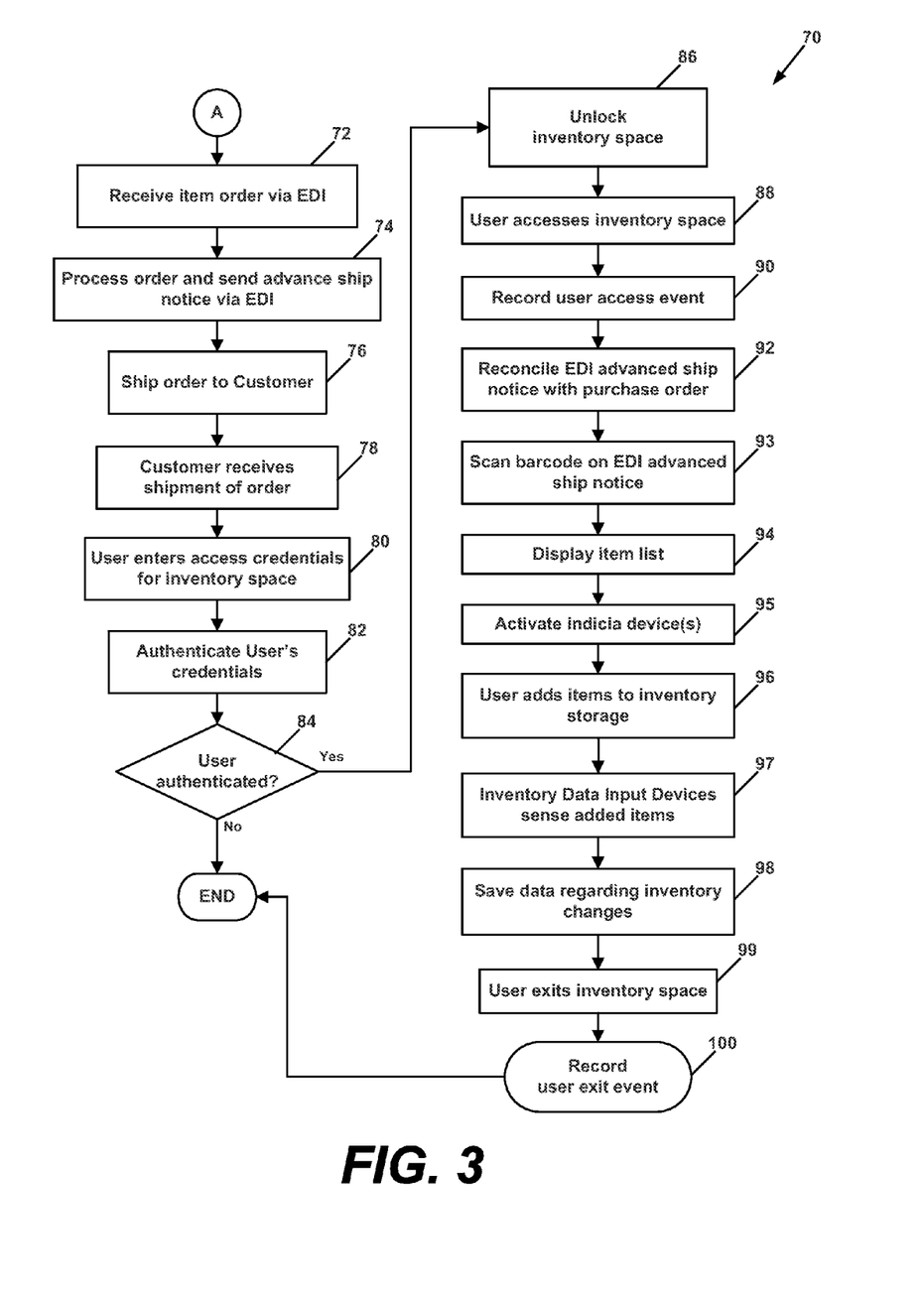

FIG. 3 depicts a preferred embodiment of a process 70 for replenishing items in the inventory space of the customer facility. Initially, the Service Provider's inventory server application 32 receives the order for items (step 72) that was placed by the inventory client application 20 in step 68 of FIG. 2. The inventory server application 32 passes the order to the EDI server 34. The EDI server 34 processes the order and sends an advance ship notice to the customer via the inventory server application 32 (step 74). The Service Provider then ships the ordered items (step 76) and the customer receives the ordered items (step 78). The customer user then takes the received items to the inventory space to restock the inventory. The customer user enters credentials for gaining access to the inventory space (step 80), such as by swiping a magnetic stripe on an ID card through a card reader of the inventory space access control system 22. The inventory client application 20 running on the customer computer 18 authenticates the user's credentials (step 82) as described above.

If the user's credentials are not authenticated (step 84), the door or entry port of the inventory space remains locked and no further action is taken, other than to log a failed entry attempt. If the user's credentials are authenticated, the inventory client application 20 executes a command to unlock the inventory space door or entry port (step 86) and the user may access the inventory space (step 88). The inventory client application 20 then updates a user entry log to record this user access event, with the date and time of access and the name/ID number of the user (step 90). Alternatively or in addition, the inventory server application 32 may update a user access log maintained on the service provider server 30.

The user reconciles the EDI advance ship notice with the purchase order that was issued in step 68 of FIG. 2 (step 92). In a preferred embodiment, this process includes scanning a barcode or other unique identifier on the EDI advance ship notice (step 93), at which point the inventory client application 20 accesses item replenishment information, such as a list of items associated with the identified EDI advance ship notice, and displays this information on the display device 19 (step 94). Based on the item replenishment information, the application 20 also activates the appropriate inventory indicia devices 27 associated with each bin, shelf, or drawer in the inventory space to indicate which bins, shelves or drawers are to receive replenishment items, and how many items are to be put in each bin, shelf or drawer (step 95). This activation may comprise turning on or lighting up indicia devices 27 that were previously in an off condition, or causing the indicia devices 27 to flash in some manner to attract the user's attention.

When the user physically adds the replenishment items to the appropriate bins, shelves, or drawers in the inventory space (step 96), the addition is automatically sensed by one or more of the inventory sensors 24 (such as by sensing additional weight in a bin or by sensing the presence of previously unlogged RFID tags on the added items) and the corresponding replenishment data is provided to the inventory client application 20 (step 97). The inventory client application 20 records the data indicating an addition of items to inventory (step 98). In a preferred embodiment, a list of the added items is displayed on the display screen 19 for viewing, confirmation, and editing by the user. When the user exits the inventory space (step 99), the inventory client application 20 logs a user exit event (step 100).

It should be appreciated that many of the steps of FIGS. 2 and 3 may be performed by the inventory server application 32, by the inventory client application 20, or by both working together. Thus, the invention is not limited to performance of the process steps by any particular application or on any particular computer system.

As shown in FIG. 1, some embodiments of the invention include a physician interface computer 15, which may be a personal computer, laptop computer, tablet/pad computer, smart phone, or other such computing device. During an examination of a patient, a physician may use the physician interface computer 15 to access and follow diagnostic/treatment protocol guidelines, record diagnostic information, record patent information, make notes, and order medical items to be dispensed to the patient as part of the patient's treatment. Preferably, the physician interface computer 15 is operable to communicate with the customer network 12 and the service provider network 14 via the Internet 16 or other communication network. In a preferred embodiment, a physician may use the physician interface computer 15 to prescribe items in inventory that a patient needs, and send the order data for the prescribed items to the inventory client application 20 running on the customer computer 18.

As alluded to above, the physician interface computer 15 may be used to access diagnostic/treatment protocol guidelines for various types of injuries, such as orthopedic injuries. Preferably, these guidelines are provided in a web-based application that may be accessed using the physician interface computer 15 via the Internet 16. In one preferred embodiment depicted in FIG. 1, the guidelines are provided by a treatment protocol application 33 running on the service provider server 30. The guidelines may include checklists and tips for diagnosis, treatment, documentation, and billing for various types of injuries. Preferably, the guidelines include a list of related medical items, such as DMEPOS items, that can be dispensed for treatment of a diagnosed injury. These items can be ordered via the service provider network 14 and the EDI server 34.

In some embodiments, the treatment protocol application 33 displays listings on the physician interface computer 15 of reimbursement billing codes and diagnostic codes associated with the types of injuries covered by the guidelines. The billing codes indicate Medicare-reimbursable amounts for the examination and for the medical items prescribed for treatment. The diagnostic codes (also referred to as ICD codes) identify the type of injury.

In a preferred embodiment, the treatment protocol application 33 also displays listings of medical items that may be ordered from the Service Provider for treatment of the particular diagnosed injury, with links for directly ordering the items. For example, for an orthopedic ankle injury, the treatment protocol application 33 may display a listing of available ankle braces, ankle stirrups and walking boots. The items are preferably listed in groups according a product code, such as Healthcare Common Procedure Coding System (HCPCS) codes.

In addition to ordering medical items from the Service Provider for replenishing inventory, preferred embodiments of the treatment protocol application 33 allow the physician to use the physician interface computer 15 to dispense an item from inventory at the doctor's office or clinic. In this embodiment, the treatment protocol application 33 generates and sends item dispensing information, which may include a product code for the item to be dispensed, a patient identifier, and a billing code to the inventory client application 20. Based on the item dispensing information, the inventory client application 20 displays information on the display device 19 indicating the item to be dispensed, the bin, shelf or drawer where the item may be found in the inventory space, and patient identification information. Preferably, the inventory client application 20 activates the appropriate inventory indicia device 27 to indicate the bin, shelf or drawer where the item is located in the inventory space.

In one embodiment, when the physician uses the treatment protocol application 33 to dispense a particular medical item for a patient, the treatment protocol application 33 verifies that the HCPCS code identifies an item that is appropriate for treatment of the injury or condition indicated by the diagnostic code entered in the patient's record. If the item is not appropriate, the treatment protocol application 33 displays a message prompting the physician to double check that the correct item is being dispensed for treatment of the particular injury.

Although some embodiments of the invention are directed to dispensing, billing and inventory management for DMEPOS items, the apparatus and methods described herein are also applicable to dispensing, billing and inventory management of other types of medical items, such as surgical implant items and items used in a catheter lab. Thus, "medical item" as that term is used herein is not limited to DMEPOS items or any other particular type of medical item.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An inventory system for managing information regarding medical items dispensed in conjunction with medical treatment of patients of a medical facility, wherein the medical items have RFID tags attached thereto that identify the medical items to which the RFID tags are attached, the inventory system comprising:
   a secured limited-access inventory space in which the medical items are stored;
   a door for providing user access to the inventory space; and
   an inventory management system provided by an inventory management service provider, which is an entity that provides the inventory management system for use by the medical facility and that is also a medical item supplier for the medical facility, the inventory management system comprising:
      an inventory access control system comprising an entry-access device that authorized personnel use to enter credentials for gaining access to the inventory space;
      one or more RFID sensors for sensing the presence of RFID tags attached to medical items in the inventory space and for sensing removal of one or more medical items from the inventory space to be dispensed to a patient, and for generating item usage information indicative of an identity and quantity of the one or more medical items removed;
      one or more computers in communication with the one or more RFID sensors and the inventory access control system, the one or more computers configured to store and manage the item usage information and billing information for the one or more medical items dispensed to the patient;
      an authorized user database in communication with the one or more computers for storing records for authenticating the credentials of personnel seeking access to the inventory space;
      one or more databases in communication with the one or more computers, the one or more databases for storing the billing information including:
         information regarding the patient, medical insurance providers and medical item suppliers, wherein the medical item suppliers are entities that supply medical items to the medical facility, and wherein the medical insurance providers are entities that pay for medical expenses incurred by patients of the medical facility;
         information that associates the patient with a medical insurance provider to which medical expenses incurred by the patient are to be billed;
         information that associates various medical item suppliers as preferred billers for various medical insurance providers, wherein a preferred biller is a medical item supplier that a medical insurance provider prefers to pay for medical expenses incurred by a patient, wherein a preferred biller may be the inventory management service provider or another of the medical item suppliers, and wherein the billing information may indicate that a preferred biller is an entity other than the inventory management service provider; and
      one or more software applications executed on the one or more computers associated with the medical facility, the one or more software applications including computer-executable instructions which, when executed:
         compare the credentials entered using the entry-access device to the records stored in the authorized user database, and upon authentication of the credentials, send a command to unlock the door of the inventory space;
         upon the RFID sensors sensing removal of the medical items from the inventory space, associate the item usage information of medical items removed from the inventory space with information identifying the personnel that removed the medical items from the inventory space, thereby providing for user accountability for the removed medical items;
         associate the item usage information with patient information that identifies the patient to which the one or more medical items are dispensed;
         process the billing information to identify a medical insurance provider to which medical expenses incurred by the patient are to be billed;
         access the one or more databases to identify a medical item supplier that is the preferred biller for the patient's medical insurance provider;
         determine whether the inventory management service provider is the medical item supplier identified as the preferred biller for the patient's medical insurance provider;
         generate an invoice from the inventory management service provider to bill the patient's medical insurance provider when it is determined that the inventory management service provider is the preferred biller for the patient's medical insurance provider; and
         send the billing information to the medical item supplier identified as the preferred biller for the patient's medical insurance provider when it is determined that the inventory management service provider is not the preferred biller for the patient's medical insurance provider.

2. The inventory system of claim 1 wherein the one or more software applications include computer-executable instructions which, when executed, generate a billing-only invoice directed to the medical item supplier identified as the preferred biller for the patient's medical insurance provider when it is determined that the inventory management service provider is not the preferred biller for the patient's medical insurance provider, wherein the billing-only invoice is to be paid to the inventory management service provider.

3. The inventory system of claim 1 wherein the one or more computers comprise a customer computer associated with the medical facility and a service provider computer associated with the inventory management service provider that is in communication with the customer computer through a communication network, and wherein the one or more software applications are executed on one or both of service provider computer and the customer computer.

* * * * *